United States Patent [19]

Baker

[11] Patent Number: 4,781,200

[45] Date of Patent: Nov. 1, 1988

[54] AMBULATORY NON-INVASIVE AUTOMATIC FETAL MONITORING SYSTEM

[76] Inventor: Donald A. Baker, Box 4414, Polson, Mont. 59860

[21] Appl. No.: 784,663

[22] Filed: Oct. 4, 1985

[51] Int. Cl.$^4$ ................................................ D61B 5/04
[52] U.S. Cl. ................................. 128/670; 128/698; 128/115; 128/775; 128/706
[58] Field of Search ............... 128/661, 671, 698, 775, 128/778, 782, 706

[56] References Cited

U.S. PATENT DOCUMENTS

| | | | |
|---|---|---|---|
| 3,561,430 | 2/1981 | Filler, Jr. et al. | 128/661 |
| 3,780,726 | 12/1973 | Hatks | 128/661 |
| 4,086,917 | 5/1978 | Burks et al. | 128/661 |
| 4,211,237 | 7/1980 | Nagel | 128/715 |
| 4,299,234 | 11/1981 | Epstein et al. | 128/715 |
| 4,367,752 | 1/1983 | Jimenez et al. | 128/706 |

FOREIGN PATENT DOCUMENTS

| | | | |
|---|---|---|---|
| 48001 | 1/1980 | European Pat. Off. | 128/698 |
| 48103 | 3/1981 | Japan | 128/698 |
| 2121967 | 1/1984 | United Kingdom | 128/698 |

*Primary Examiner*—William E. Kamm
*Attorney, Agent, or Firm*—Wells, St. John & Roberts

[57] ABSTRACT

Fetal monitors for automatically and continuously monitoring the well-being of a fetus. The preferably ambulatory monitors include one or more fetal cardiac sensors for detecting the fetal heart rate. The sensors can be acoustic, electrocardiographic or bioimpedence types. Interference sensors are included for selectively sensing the principle interference components contained in the fetal cardiac sensor signals. The preferred microprocessor based signal processing system converts the sensor signals into digital format and transforms the signals from time domain into frequency domain and back into time domain after appropriate processing. Adaptive cancellation of interfering signals and other signal enhancing operations are disclosed. Analytical subsystems continuously analyze the fetal heart rate information and information from a fetal movement sensor to perform a fetal non-stress test. Subsystems for other analytical tests are also disclosed. Alarms warn the mother when fetal behavior is outside of preprogrammed acceptable limits of such analytical tests so that remedial action may be initiated. The monitoring system also preferably includes a sensor belt for properly and conveniently wearing the sensors and a control unit containing the signal processing and related components.

29 Claims, 8 Drawing Sheets

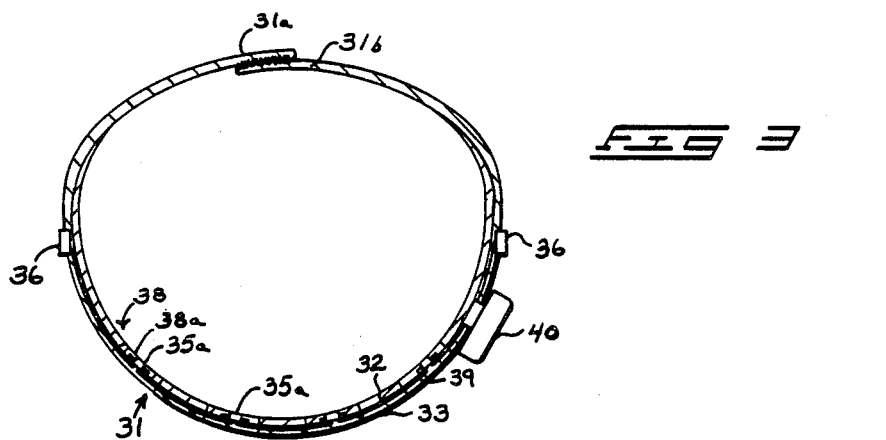
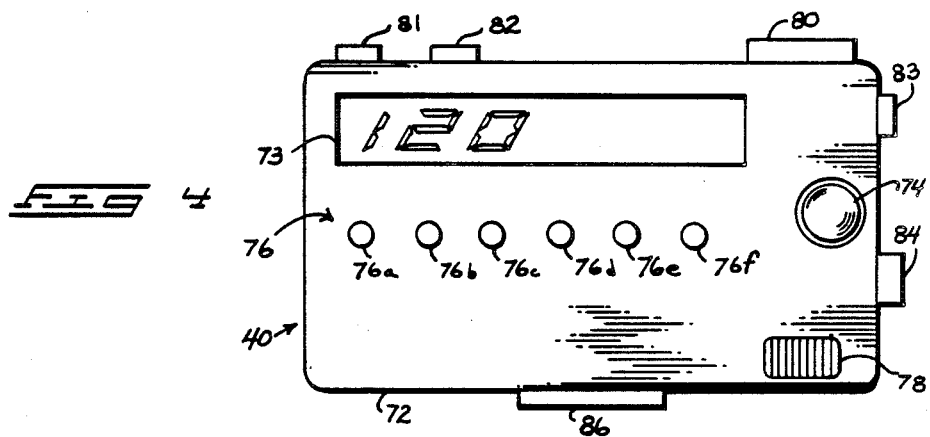
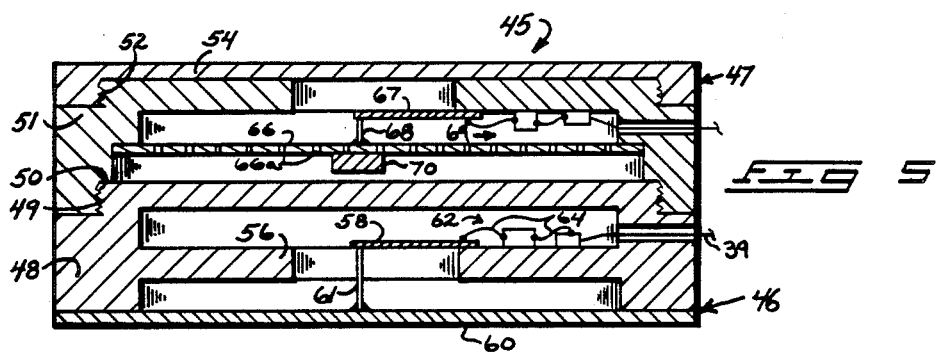

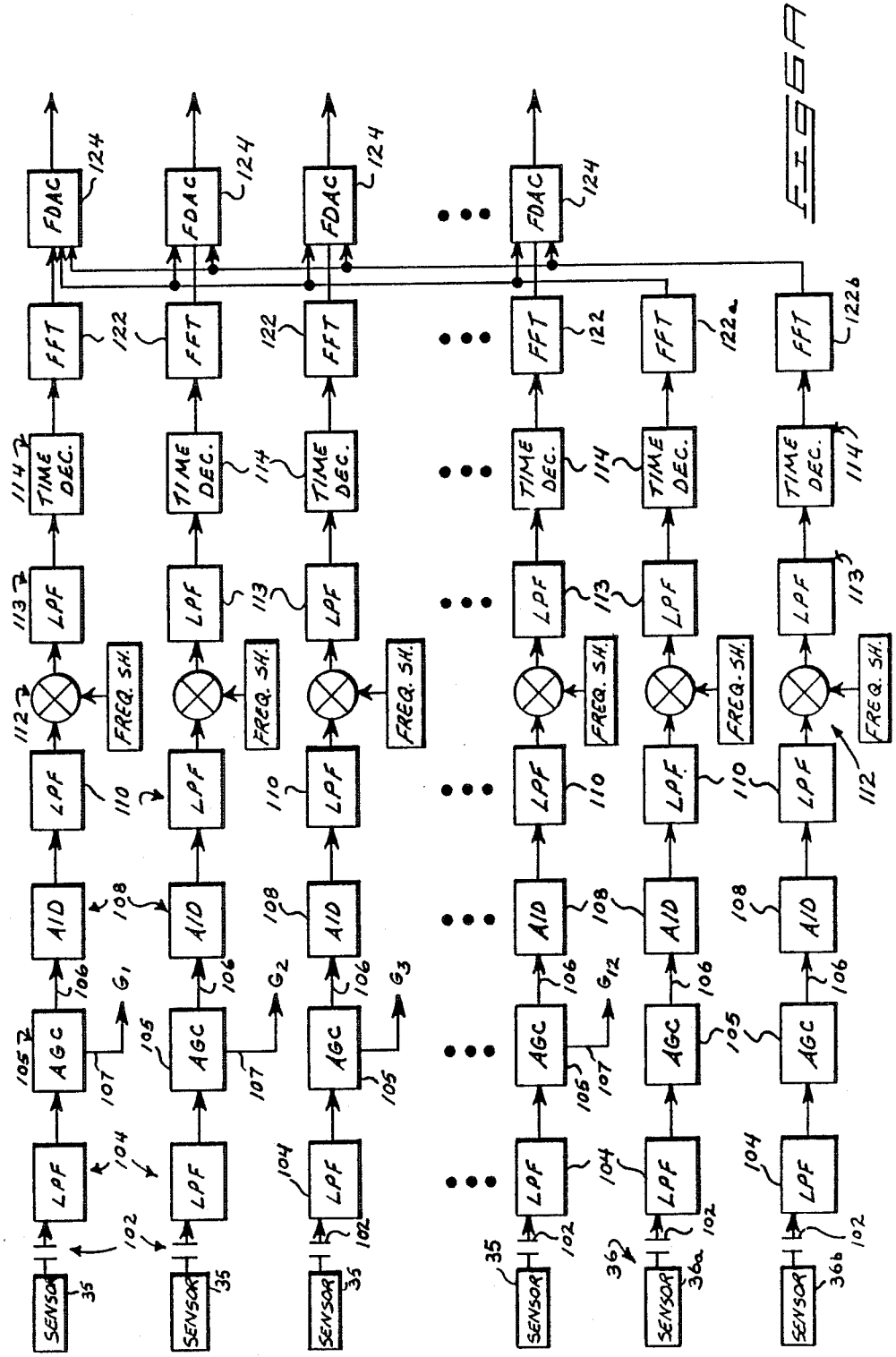

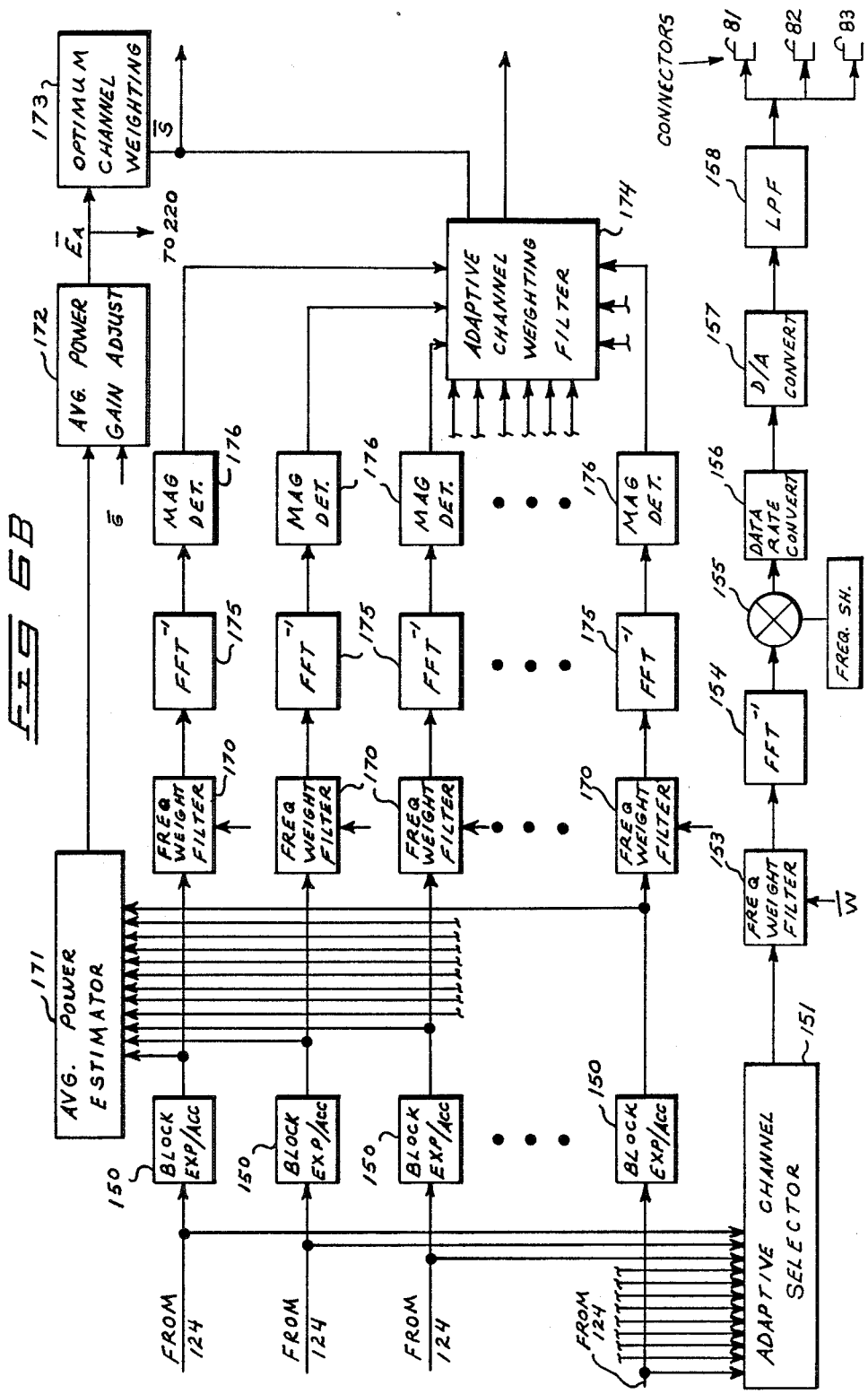

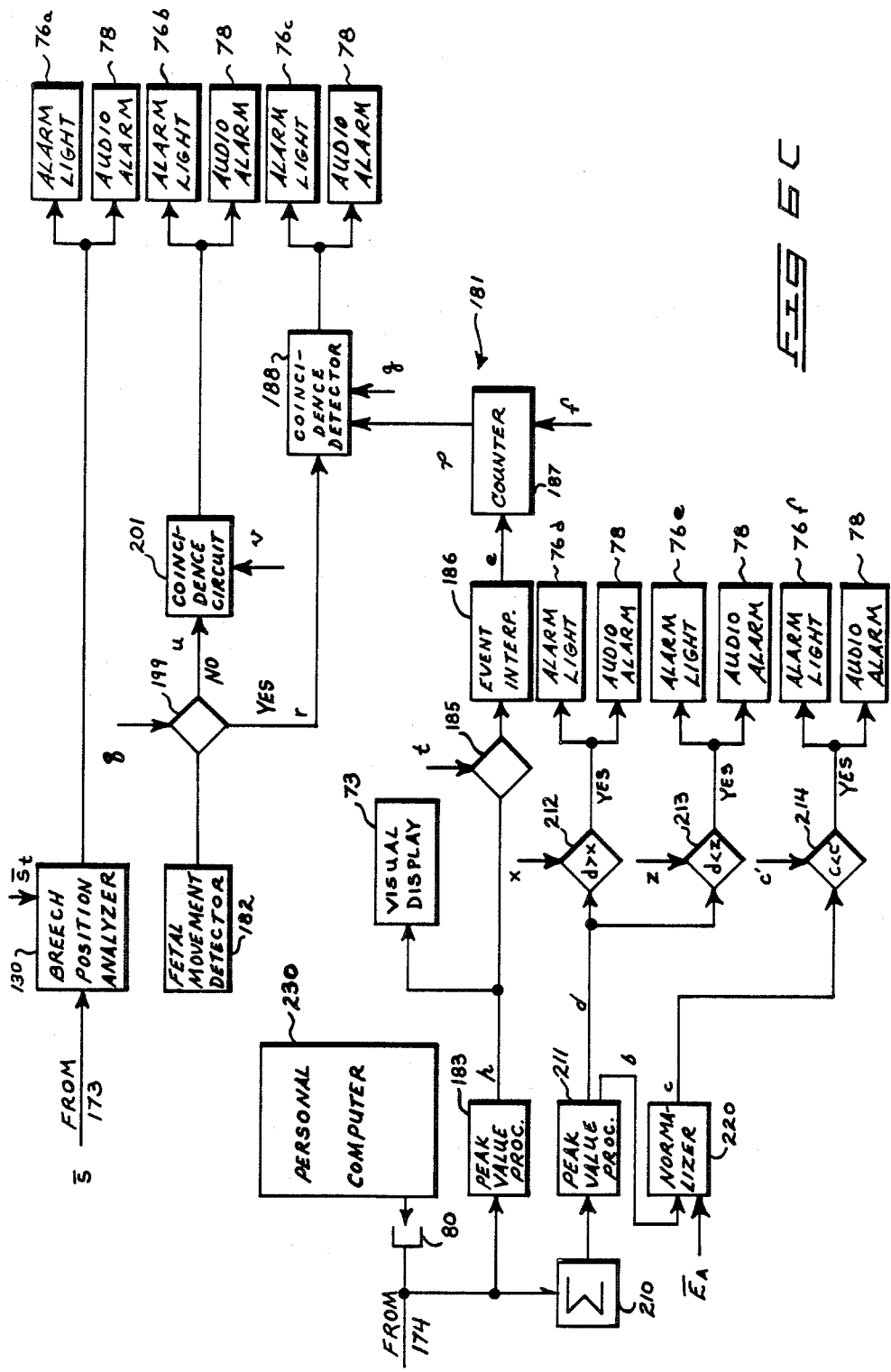

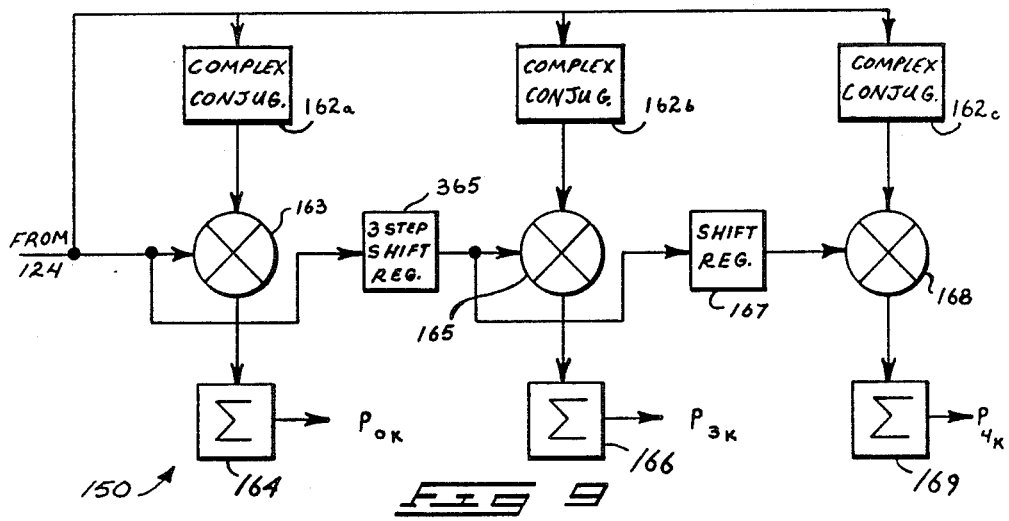
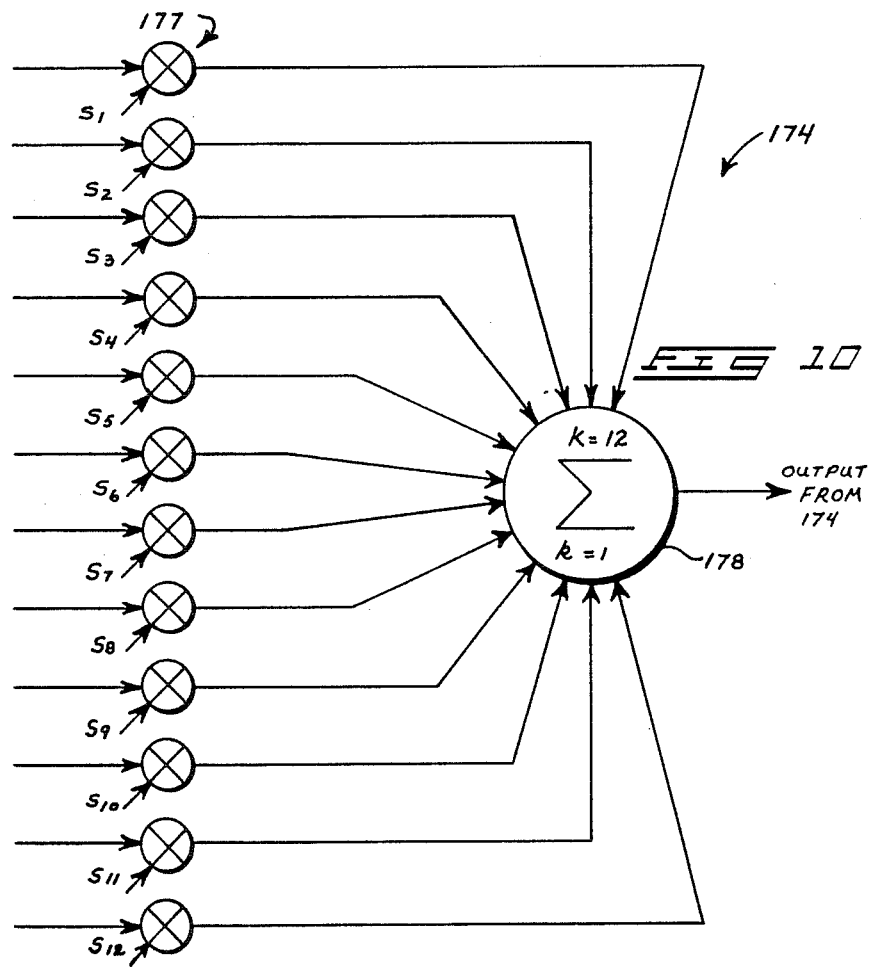

4,781,200

AMBULATORY NON-INVASIVE AUTOMATIC FETAL MONITORING SYSTEM

TECHNICAL FIELD

The technical field of this invention is apparatus for monitoring the well-being of fetuses.

BACKGROUND OF THE INVENTION

The difficulties in monitoring fetal well-being have long been recognized by the medical profession. The position of the fetus within the womb, surrounded by the amnion and amniotic fluid makes direct examination of the fetus impossible or very difficult using most examination techniques.

Traditional methods for examination of fetuses have included using a stethoscope to listen to the fetal heartbeat, and physical examination by palpatation of the female anatomy surrounding the fetus. Although these techniques are useful they are limited in the amount of information derived. They are also performed during relatively short periods of time during a visit to the physician's office. Accordingly, they do not provide sufficient information concerning the health of the fetus in response to varying environmental conditions and unexpected occurrences confronting the mother and fetus.

Other techniques for determining fetal conditions include the use of ultrasound. The ultrasound techniques generally use an apparatus which includes an ultrasonic transducer which generates ultrasonic vibrations which are directed at the fetal heart or other organs. Ultrasonic waves reflect off of the anatomical parts of the fetus and are sensed by an appropriate sensor and processed to determine the frequency shift associated with reflection from the moving fetal heart valve according to the well-known Doppler Principle. The information gained by such techniques is then analyzed and integrated to provide information about the fetus, including fetal heart rate. Such testing equipment is costly and is usually used by hospitals and other public health facilities. The high cost also limits the amount of time any one fetus can be monitored. Such equipment is also relatively large and bulky and has not been developed into a portable system which can be used to monitor fetal well-being while the mother functions in her normal life. Accordingly, such nonambulatory equipment has not been satisfactory for use in medical studies seeking to determine effects on the fetus of various environmental and behavioral factors, and health patterns experienced or practiced by the mother.

Ultrasound techniques for determining fetal heart rate are also disadvantageous because they are invasive in nature, applying a stream of high frequency ultrasonic vibration to the developing fetus and fetal heart valve. Such invasive properties may have significant detrimental effects on the fetus. They further require a relatively tedious alignment of the ultrasonic transducer with the fetal heart. Even moderate movement of the patient often results in erroneous readings and increased examination time and costs.

Prior art includes several types of fetal monitors. An early fetal heart monitor is described in U.S. Pat. No. 2,536,527 to Appel. The Appel invention was designed for monitoring fetal condition during delivery. A microphone communicates with a stethoscope to produce a signal which is amplified, filtered, rectified and used to control two relays which indicate abnormally high or low heart rates or amplitudes of the fetal heart.

U.S. Pat. No. 3,187,098 to Farrar et al discloses a fetal heartbeat detector. The Farrar detector uses a cantilevered piezoelectric crystal mounted within a contacting slab so as to have a natural frequency of approximately greater than 50 Hz.

Another fetal monitor is shown in U.S. Pat. No. 3,409,737 to Settler et al. The Settler monitor is used with a belt having three spaced microphones. A three stage amplification circuit is used to selectively amplify the fetal heartbeat and remove the maternal heartbeat.

U.S. Pat. No. 3,599,628 to Abbenante et al discloses a device for monitoring fetal heartbeat and intrauterine pressure for the purpose of correlating these two parameters and indicating fetal distress therefrom. A catheter is inserted into the uterus and is liquid coupled to a piezoelectric pressure transducer to determine the intrauterine pressure. A probe is attached directly to the fetus to measure the fetal ECG. Such a system is only practical for use during delivery.

U.S. Pat. No. 3,703,168 discloses a fetal heart monitor having electrodes which are positioned against the skin of the mother to derive an electrical signal therefrom. A fetal ECG is derived from the electrode signal as is a signal indicative of maternal contractions.

A further fetal monitor used to detect intrauterine contractions and fetal heart rate is described in U.S. Pat. No. 3,989,034. An indication of fetal distress is derived therefrom.

Sureau et al discloses a fetal heart rate apparatus useful during labor to measure the decelerations in fetal heart rate during uterine contractions (U.S. Pat. No. 4,027,057).

U.S. Pat. No. 4,299,234 to Epstein et al discloses a fetal heart rate monitor which combines electrocardiogram and electromyogram types signals to increase the reliability and accuracy of the resulting heart rate information.

Prior art fetal monitors have been limited in their usefulness because of their typical sole function of analyzing an input signal to determine fetal heart rate. Some have also utilized the intrauterine pressure parameter as a further indicator fetal stress. However, none are designed to provide an ambulatory monitor which can continuously and automatically analyze fetal well-being using more complex analyses based upon heart rate patterns and movements of the fetus.

Absence of such an ambulatory fetal monitor from the prior art has made it impossible to effectively monitor and warn the mother of many health risks to the fetus, such as caused by maternal activities such as smoking, drinking or drug consumption. Any current testing directed to these problems must be done in a clinical setting which does little or nothing to help the large number of untested mothers to recognize the problem and is of depreciated scientific value because of the differences in consumption patterns and activity as compared to the patients normal lifestyle. Such clinical testing is also limited since more subtle variations in lifestyle can also not be explored as significant factors to determine the effects on fetal well-being.

In addition to the recognized risks associated with alcohol, tobacco and drug consumption, there are additional environmental factors and activities which may have a discernible effect on fetal well-being. Investigation of such factors as exposure to industrial, agricultural and laboratory chemicals may be of particular importance. Toxic chemical exposure in the home may be of even greater importance. High levels of activity such as running, cycling, aerobics and hiking may also have discernible effects on the fetus, but cannot currently be effectively tested. The effect of stressful situations and maternal emotional traumas upon fetal well-being may also be investigated with a continuous ambulatory fetal monitor whereas prior art clinical monitors cannot be effectively used. The effects on the fetus of maternal infections from viral and bacterial pathogens may also be investigated in an accurate and reliable manner when continuous monitoring during routine life is made possible.

A continuous ambulatory fetal monitor is also advantageous for use with mothers having a higher risk of pregnancy-related complications. Such an ambulatory monitor can provide additional peace of mind not otherwise available for such patients, and can potentially mean the difference between life and death in critical circumstances.

BRIEF DESCRIPTION OF THE PREFERRED EMBODIMENT

The present invention provides a selfcontained, lightweight ambulatory fetal monitoring system capable of substantially continuous analysis of fetal well-being. The monitor includes a sensor garment which is worn by the mother and has a plurality of sensors. The sensors detect fetal heartbeats and movements of the fetus within the mother. Signals developed by the sensors are processed by signal processing equipment and analyzed by a programmable data processing unit which can be provided with a variety of analytical programs which automatically and continuously analyze fetal well-being. The processing unit is used to control alarms which indicate when fetal behavior has varied outside of preprogrammed limits.

BRIEF DESCRIPTION OF THE DRAWINGS

A preferred embodiment of the invention is illustrated in the accompanying drawings, in which:

FIG. 3 is a cross-sectional view of the sensor belt of FIGS. 1 and 2 arranged in a circumferential band as worn and without the mother;

FIG. 4 is a front elevational view of the control unit shown in FIG. 1;

FIG. 5 is an enlarged longitudinal sectional view of one sensor type which may be used in the fetal monitoring system of FIG. 1;

FIGS. 6A, 6B, and 6C are interrelated schematic drawings of a preferred signal processing architecture used in the system of FIG. 1;

FIG. 9 is a schematic drawing of one form of digital architecture useful in performing the block expansion and accumulation steps shown in the system of FIGS. 6A-6C;

FIG. 10 is a schematic drawing of one form of digital architecture useful in performing the adaptive channel weighting filter operation shown in the system of FIGS. 6A-6C.

DETAILED DESCRIPTION OF THE PREFERRED EMBODIMENT

In compliance with the constitutional purpose of the Patent Laws "to promote the progress of science and useful arts" (Article 1, Section 8), applicant submits the following disclosure of the invention.

Figure 1:
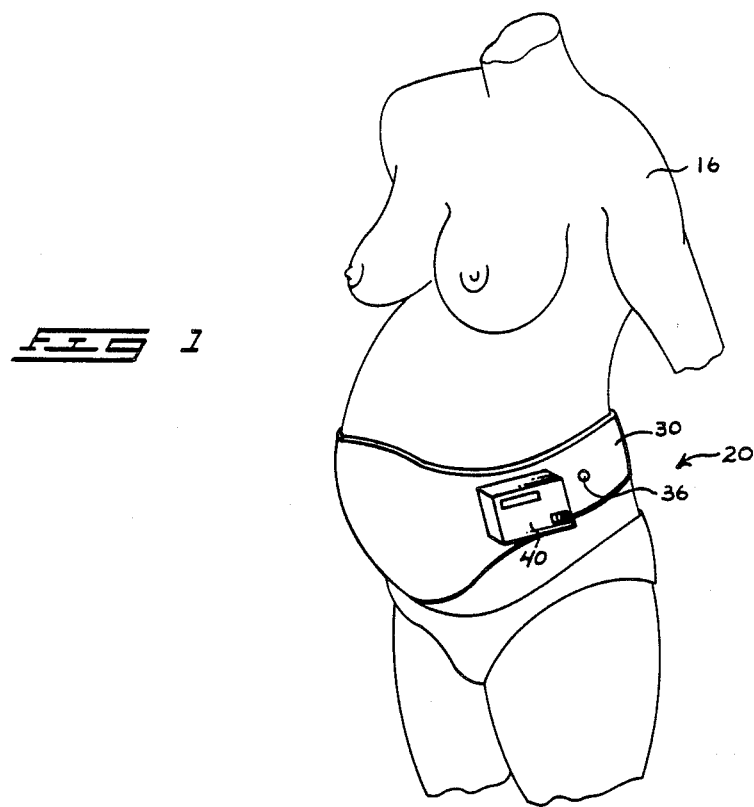
FIG. 1 is a perspective view showing a human mother wearing a fetal monitoring system according to this invention.

FIG. 1 shows a human mother 16 wearing a fetal monitoring system 20 constructed according to this invention. Fetal monitoring system 20 includes a sensor belt 30 and a control unit 40.

Figure 2:
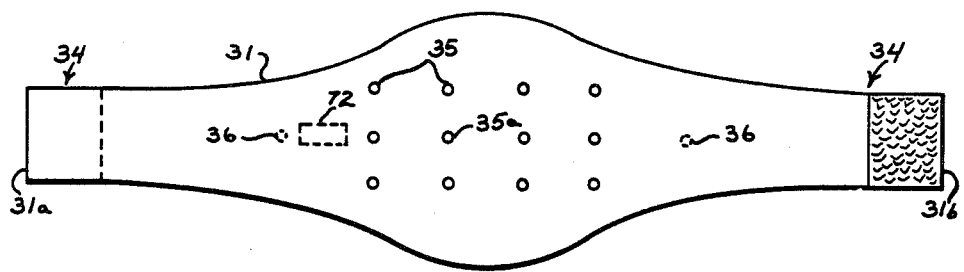
FIG. 2 is an elevational view of the sensor belt shown in FIG. 1 in a flattened or unrolled condition.

FIGS. 1 and 2 show that sensor belt 30 includes an appropriately shaped belt piece 31 which is made from a piece or pieces of flexible, expandable material which can easily accommodate the curves of the maternal midsection during the later stages of pregnancy. The belt piece has an enlarged abdominal area adapted to extend over substantial portions of the mother's abdomen and position sensors adjacent thereto. FIG. 3 shows that belt piece 31 is preferably constructed to include an inner layer 32 and an outer layer 33. Both layers 32 and 33 can be made from a stretchable material such as sold under the trademark LYCRA SPANDEX. Other alternative materials are also possible. A hook and loop or other type of closure 34 is advantageously provided to join ends 31a and 31b of the belt piece together. Sensor belt 30 is designed for closure 34 to be positioned at the back during use. Belt piece 31 is elongated and designed to extend about the mother's torso along a girth extending longitudinally between the ends.

Sensor belt 30 also includes a plurality of fetal cardiac monitoring sensors 35 mounted to belt piece 31 in an appropriate arrangement. Sensor belt 30 is shown with twelve sensors 35 mounted in an approximately rectangular matrix with spacings of approximately 2-3 inches (50-75 mm) between adjacent sensors. Sensors 35 have contacting surfaces 35a which face inwardly and directly and non-invasively contact the maternal abdomen. Sensors 35 can be mounted in sensor belt 30 using any suitable mounting structure such as a sewn-in pocket 38 formed between the inner and outer layers 32 and 33 and having a pocket mouth 38a through which the contacting surfaces 35a extend. Alternative mountings for sensors 35 are clearly possible and well known in the art.

Sensor belt 30 further includes at least one embient noise or similar interference sensor or sensors 36a and 36b which can be mounted similarly to sensors 35. When interference sensors 36 are acoustic they are preferably mounted to belt pieces 31 so that they are at the sides of the mother during use. Acoustic sensors 36 are also preferably oriented with their sensory surfaces extending outwardly to sense extraneous noise.

Sensors 35 and 36 are connected to lead wires 39 which are preferably provided with a jack (not shown) into which control unit 40 is electronically connected to provide the sensor signals thereto. Lead wires 39 are advantageously routed between the inner and outer layers 32 and 33 of belt piece 31.

Sensors 35 and 36 are advantageously acoustic sensors of the types explained below. They can alternatively be electrocardiographic sensors or bioimpedence type sensors as will also be explained more fully below.

FIG. 5 shows a combined sensor 45 all or part of which can be used as the fetal monitoring sensors 35 of FIGS. 1–3. Sensor 45 includes an acoustic sensor 46 and an accelerometer 47 which are adapted for connection together. The use of accelerometer 47 is as a fetal movement sensor as will be explained more fully hereinafter. Acoustic sensor 46 includes a frame 48 which is advantageously provided with male threads 49 which are threadably receivable within female threads 50 formed in frame 51 of accelerometer 47. Accelerometer frame 51 is further advantageously provided with male threads 52 at the opposite end thereof for receiving a threaded cap 54. Cap 54 can alternatively be installed directed upon threads 49 where acoustic sensor 46 is to be used without accelerometer 47.

Acoustic sensor frame 48 advantageously includes an annular extension 56 which extends inwardly to support a cantilevered piezoelectric crystal 58. The distal end of crystal 58 is connected to the centerpoint of a flexible circular diaphragm 60 using a substantially rigid strand or fiber 61. Any desired filtering, preamplifying or other electronic components 62 desired for coupling the output of crystal 58 to control unit 40 can be mounted upon annular extension 56. Conductors 64 extend between crystal 58 and components 62. Lead wires 39 extend from components 62.

Accelerometer 47 includes a diaphragm 66 which is perforated with a plurality of holes 66a to prevent undesirable response to acoustic vibrations which might be transmitted through acoustic sensor 46. Accelerometer 47 has a piezoelectric crystal 67 which is mounted to frame 51 in a cantilevered arrangement, and is also connected at its distal end to diaphragm 66 using strand 68. Any desired preamplification, signal enhancing, or coupling electronics 69 can be mounted within frame 51 and connected to crystal 67. An end mass 70 is connected at the center point of diaphragm 66 to provide proper dynamic response for the combined mass, diaphragm and crystal mechanism.

Acoustic sensor 46 is suitable for detecting acoustic vibrations passing from the fetal heart through the mother's abdomen so that a proper signal can be obtained indicating the fetal heartbeat. The fetal heartbeat has been found to produce acoustic vibrations predominantly in the frequency range of 50–110 Hz. The maternal heartbeat produces acoustic vibrations which are primarily below 50 Hz. Accordingly, acoustic sensor 46 is designed to provide dynamic response which is most sensitive to fetal frequencies while minimizing response to maternal frequencies in order to initially minimize one of the primary sources of unwanted acoustical noise.

Although acoustic transducer 46 has been found acceptable, it may be desirable to employ other alternative acoustical electrical transducers which are either currently available or hereafter discovered, in order to optimize the performance of fetal monitoring system 20 or other forms of the invention.

Alternative accelerometer or other types of fetal movement detectors can also be substituted in lieu of accelerometer 47. Examples of potential alternative fetal movement sensors include the moving coil sensor described by David Adler and Yona Mahler in an article entitled, "Measurement of Fetal Movements by Moving-Coil Transducer", printed in *IEEE Transactions Of Biomedical Engineering*, Vol. BME-27, No. 12, December 1980, at pp. 738–740, which is hereby incorporated hereinto by reference. A further alternative fetal movement sensor is described by Eliahu Sadovsky et al in an article entitled, "Fetal Movements Recorder, Use and Indications", printed in *International Journal of Gynecology and Obstetrics*, Vol. 15, pp. 20–24, 1977, which is hereby incorporated hereinto by reference. Modifications to the signal processing equipment hereinafter described may be needed to successfully incorporate such alternative movement sensors, as will be obvious to one of skill in the art.

Acoustic sensor 46 is advantageously used as a fetal heartbeat sensor 35 in this invention. It will be readily apparent to those skilled in the art that alternative types of fetal heartbeat sensors can be used in substitution or combination with acoustic sensor 46. One available alternative fetal monitoring sensor type is the electrocardiographic type of sensor or electrode. Preferred electrocardiographic sensors include karaya or other natural gum conductive pads laminated to a thin metalized backing, such as those sold by Lectec Corp. under the trademark Tracets.

Other alternative fetal heartbeat sensor types include the bioimpedence type sensors such as acceptable for use in a system such as described in U.S. Pat. No. 4,450,527 to Sramek, which is hereby incorporated by reference hereinto.

The specific number, type and arrangement of fetal heartbeat sensors 35 used in fetal monitoring systems according to this invention will vary depending on the specific heartbeat sensing scheme employed, eg. acoustic, electrocardiographic or bioimpedence. The sensor belt 30 described herein is specifically designed for use with a plurality of acoustic sensors such as 46 and at least one fetal movement sensor, such as accelerometer 47. Suitable modifications to sensor belt 30 may be needed to affectuate the alternative fetal heartbeat sensing schemes.

Sensor belt or garment 30 is advantageously provided with a means for attaching control unit 40 thereto such as connection bar 72. Connection bar 72 receives an interengaging clip (not shown) mounted on the back of control unit 40 so that the control unit is conveniently mounted for normal wear but is readily available for viewing and detachment, and is sufficiently close to warn the mother. Control unit 40 can be provided with a vibratory alarm system for deaf mothers which suggests the desirability of mounting control unit 40 adjacent the belt so that relatively low power vibrators can be used to communicate directly via tactile vibratory contact to the mother's abdomen. Control unit can alternatively or concurrently be provided with a wristband or other means (not shown) for wear upon the mother's wrist.

FIG. 4 shows a front elevational view of a preferred controll unit 40 used in fetal monitoring system 20. Control unit 40 includes a case 72 which encloses electronic circuitry and related components. Control unit 40 further includes an appropriate display 73 which is used to provide a visual digital display of fetal heart rate and can further display information such as patient's name, due date, blood type, Rh factor, antibody screen results, VDRL, rubella titre and other desired information from a programmable memory. Such information and signal processing are performed in a digital microprocessor 300 (FIG. 11) and related memory 301 having the signal processing architecture described fully below. The patient information display and signal processing functions are performed according to well known microprocessor and microcomputer technology in which the desired patient information can be encoded using a personal computer 230 (FIG. 6c) and stored in memory 301 in unit 40. The information is easily displayed by activating the display control switch 74 which advances the display mode through a preprogrammed set of patient statistics.

Control unit 40 further includes an array of alarm lamps 76 which are advantageously a set of light emitting diodes or other light emitting devices from which the mother can visually identify the type of diagnostic test which indicates concern for fetal well-being. A variety of preprogrammed tests or analyses can be run depending upon the specific parameters of fetal well-being which are preprogrammed and used. Control unit 40 as described herein is designed to perform the following analyses:

(1) determine and display fetal heart rate;
(2) detect failure of fetus to experience heart rate increase in reaction to fetal movement, commonly called fetal reactive non-stress test;
(3) detect sustained low fetal heart rate (fetal bradycardia syndrome);
(4) detect sustained high fetal heart rate (fetal tachycardia syndrome);
(5) detect sustained absence of fetal movement (fetal movement syndrome);
(6) detect multiple fetuses; and
(7) detect breech position of fetus.

The specific parameters used in these tests will be discussed below in connection with the specific signal processing architecture used to carry out the analysis. Using suitable programming additional analysis such as the well known short term fetal heart variability and the long term fetal heart rate variability profiles can also be used.

FIG. 4 further shows an audio alarm or buzzer 78 used to audibly warn the mother or other monitoring individual when an analysis has indicated concern and the associated alarm lamp 76 has been illuminated. A vibratory coil or other element (not shown) is also advantageously included and connected to warn deaf individuals.

Control unit 40 is provided with a sensor input jack 86 into which signals from sensors 35 and 36 are conveyed. Control unit 40 is further provided with an appropriate programming interface jack 80 for connecting a suitable programming device such as personal computer 230 or other microprocessor programmer as is well known in the art of digital equipment. A telephone loop jack 81, and audio phone jack 82 are also advantageously included to allow the processed fetal heart sounds to be communicated via telephone or through a sound amplification system for family and friends to share the excitement of the expected baby. A tape recorder jack 83 can further be provided to allow tape recording of the fetal sounds. A battery recharging jack 84 is further provided to allow recharging of control unit batteries 305.

Figure 11:
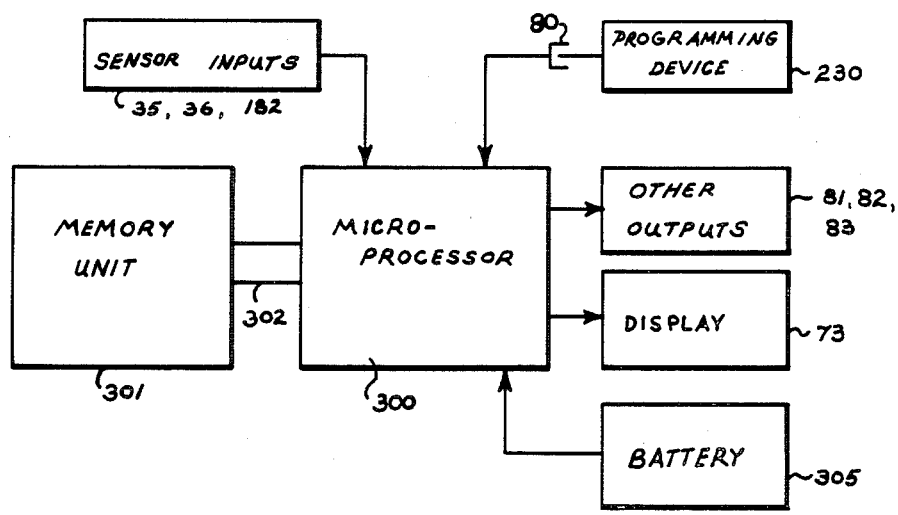
FIG. 11 is a block diagram showing electronic components of a preferred fetal monitoring system according to this invention.

FIGS. 6A-6C together schematically show a preferred form of digital signal processing architecture 100 which can be used in the fetal monitoring system 20 according to this invention. Signal processing system 100 is the principal section of control unit 40. FIG. 11 shows the general relationship between principle hardware components which can be used to implement signal processing system 100. FIG. 11 shows sensor inputs 35, 36 and 182 connected to microprocessor 300. Memory 301 is connected via bus 302 to microprocessor 300. Input device 230 is detachably connected via jack 80 to microprocessor 300. Battery 305 is used to power microprocessor 300, memory unit 301, display 73 and other related components.

FIGS. 6A-6C show that signal processing system 100 receives input signals from one or more fetal heart sensors 35, which define fetal monitoring channels 1-12. Signals are also received from interference sensors 36 or other sensors specifically adapted and positioned to selectively sense interfering inputs. When fetal heart sensors 35 are acoustic sensors, such as sensors 46, then the principal interfering inputs occur due to auditory noise from either the mother or external sources. In such case, the sensor belt 30 is provided with similar, or preferably identical acoustic sensors 46 which are outwardly oriented and serve as interference sensors 36 mounted at the sides of sensor belt 30.

When fetal heart sensors 35 are electrocardiographic type sensors then the principal noise or interfering signal is from the electrocardiographic (ECG) potential variations occurring within the mother. The signal processing circuitry 100 can be used to adaptively cancel such interference using an interfering or cancelling signal which is predominantly composed of maternal ECG. This can be done using interfering electrodes placed adjacent to the maternal heart in an arrangement well known in connection with obtaining human electrocardiograms (not shown). Either the acoustic sensors 36, ECG or other type of interference sensors 36 can be used in signal processing system 100. Primary description given hereinafter will be with respect to use of properly oriented acoustic sensors, such as 46, in connection with both the fetal heart sensors 35 and interference sensors 36. Use of identical sensors for all fetal heartbeat sensors 35 and interference sensors 36 is preferred.

FIG. 6A indicates that each of sensors 35 and 36 are coupled to the signal processing system using series capacitors 102. Alternative coupling arrangements are also possible as dictated by the specific sensors employed and subsequent circuitry used as is well-known. Sensor preamplification circuitry such as 62 shown with acoustic sensor is not schematically shown in FIG. 6A, and may or may not necessitate further initial amplification (not shown), or special coupling into system 100.

The outputs from capacitors 102 are input into appropriate first analog low pass filters (LPF) 104, well known in the art, designed to suppress signal frequency components above 512 Hz. Low pass filters (LPF) 104 prevent unwanted high frequency noise from subsequently being encoded into digital format.

The output from low pass filters 104 are input into parallel automatic gain control circuits (AGC) 105, which are preferably identical or very similar in construction. Automatic gain control circuits 105 provide a signal output 106 which is communicated to appropriate analog-to-digital convertors (A/D) 108. Automatic gain control circuits 105 automatically sense the strength of the incoming signals from low pass filters 104 and automatically amplify the signals by individualized gains which appropriately adjust the range of the analog signals to the dynamic range of the inputs of analog-to-digital convertors 108. The automatic gain control circuits 105 associated with fetal sensor channels 1-12 also provide secondary outputs 107 which are each a gain coefficient indicative of the gain by which each individual sensor channel signal is being amplified. This gain coefficient information is used in signal processing system 100 by average power gain adjustment operator 172, hereinafter described. Automatic gain control circuits suitable for use in this invention are well known in the electronics arts. Automatic gain control circuits 105 are designed to provide a response time of approximately 8 seconds to avoid potential short term distortion of the sensor signals.

Analog-to-digital (A/D) convertors 108 can be of a variety of suitable types, well known in the art, having the desired dynamic input range. A/D convertors 108 encode the sensor signals for their respective channels into a digital format, such as a 12 bit format, at a desired sampling rate, such as 1024 samples per second.

The digital output signals from A/D convertors 108 are communicated to parallel digital single pole low pass filter operations 110 for each sensor channel. Low pass filter operations 110 can advantageously be accomplished on a centralized microprocessor 300 also used for other digital signal processing functions for system 100. Digital low pass filter operations 110 are defined by the following mathematical and operational relationship:

$$X(n+1) = X(n) - (X(n) - S(n))/4$$

where:
S(n) is the input digital signal sequence to the digital low pass filters 100;
n is an index of time and the order of the digital words produced by A/D convertors 108 at the sampling rate; and
X(n) is the output sequence of digitally encoded words representing the digitally filtered sensor signal at time n.

Digital low pass filter operators 110 perform only two different computational operations and one scale operation per sample time per channel thus minimizing the computation load placed on the microprocessor. The time response of the preferred filter operations are $h(t) = e^{-t/T}$, where $T = 1/128$ second. The frequency response of the sensor signal being filtered is $H(f) = K/(f^2 - 1/(T^2))$, where f is the input signal frequency, K is a constant for the specific system used and T is 1/128 second.

The digital low pass filter operations 110 for each channel are followed by parallel frequency downshift operations 112, parallel second low pass filter operations 113, and parallel time decimation operations 114. The frequency downshift operation is accomplished by multiplying the digital output signals from second low pass filters 113 by the complex signal $e2\pi i f_s t$; where $f_s$ is the shift frequency, t is the time variable and i represents the complex square root of $-1$. In the system 100 described herein, the desired frequency shift, $f_s$, is equal to 256 Hz. This frequency shift is desired to reduce the volume of data which must be processed by the centralized microprocessors 300 or discrete microprocessors which perform all of the indicated digital processing operations.

Figure 7:
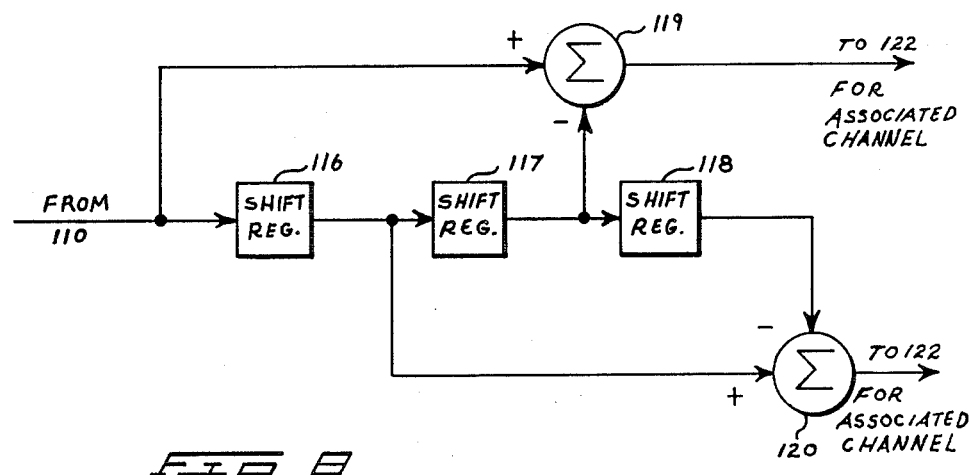
FIG. 7 is a schematic drawing of one form of digital architecture useful in performing frequency downshift, digital low pass filtering, and time decimation operations shown in the system of FIGS. 6A-6C.

The frequency downshift operations 112, second low pass filter operations 113 and time decimation operations 114 can be performed using a particularly efficient arrangement of digital elements shown in FIG. 7. FIG. 7 shows three shift registers 116, 117 and 118. Digital words from the output of first digital low pass filters 110 are input to first shift register 116 at the sampling rate of A/D convertor 108. The input to first shift register 116 is also input to a difference operator 119. The filtered digital information from 110 is sequenced through shift registers 116, 117 and 118 at the sampling rate. First difference operator 119 subtracts the output from register 117 from the input arriving to register 116 to produce the real component of the output from the combined steps 112-114. A second difference operator 120 subtracts the output from shift register 118 from the output from shift register 116, to produce the imaginary component output from the combined steps 112-114. The outputs from difference operators 119 and 120 are the resulting real and imaginary components of the channel signals for one channel and are in complex format with a complex data rate equal to one half the data input rate. Each channel is provided with the operational structure just described. In the preferred system 100, data flows into steps 112-114 at a rate of 1024 digital words per second and leaves step 114 in complex format at a rate of 512 complex words per second as the interspersed real and imaginary components from difference operators 119 and 120, respectively. The effective frequency response of steps 112-114 is sin $(2\pi fT)/2\pi fT$ where $T = 1/256$ and f is the frequency variable.

FIG. 6A shows that the outputs from operations 112-114 are input to parallel Fast Fourier Transform (FFT) operators 122 for each channel. Fast Fourier Transform operations 122 are performed using either the centralized microprocessor (not shown) or on separate Fourier transform operators well known in the art. The Fourier transform operations 122 place the complex digital information into the form of a Fourier series well known in the art. Preferred FFT operators 122 can typically accept blocks of data composed of 64 complex digital words. The Fourier transform operators 122 preferably are capable of performing a 128 point transform every ⅛ second. The block of 64 complex digital words and an additional block of 64 zeros make up the 128 points subjected to transformation. The output from the FFT operations 122 is a series of 128 complex spectral coefficients associated with the components of the Fourier series.

The block of complex spectral coefficients from Fast Fourier Transform operators 122 are input to frequency domain adaptive cancellation operators (FDAC) 124. The frequency domain adaptive cancellation operations are used to cancel out the ambient interference or background noise that is sensed by interference sensors such as 36. In the case of acoustic interference sensors 36 the background noise such as from maternal speech, singing and other ambient noise is sensed by sensors 36 and transformed into complex spectral coefficients in a process similar to the channels associated with fetal sensors 35. In the use of ECG-type fetal sensors 35, the primary interfering component of the sensor signal is the maternal ECG. The maternal ECG is sensed using ECG sensors placed to exclusively detect maternal ECG. The maternal ECG sensed by sensors 36 is processed through the FFT operations associated with the interfering sensor channels. Analogous arrangements are possible with bioimpedence based systems.

Figure 8:
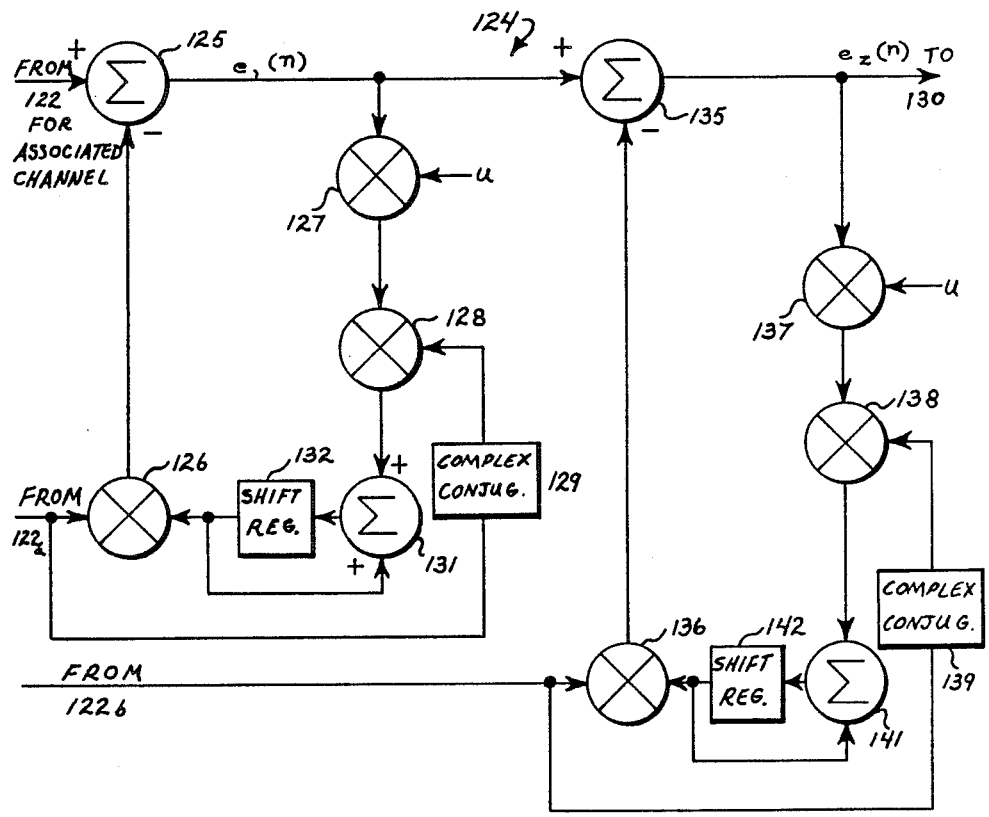
FIG. 8 is a schematic drawing of one form of digital architecture useful in performing the frequency domain adaptive cancellation (FDAC) operations shown in the system of FIGS. 6A-6C.

The output from Fourier Transform operators 122a and b, associated with interference sensors 36, are input to all of the frequency domain adaptive cancellers 124 associated with all fetal sensor channels. The frequency domain adaptive cancellation operations 124 adaptively cancel the interfering noise or signals using the digital processing architecture schematically shown in FIG. 8. FIG. 8 shows the operations performed upon each complex Fourier series spectral coefficient by each frequency domain adaptive cancellation (FDAC) operator 124).

Frequency domain adaptive cancellers 124 each receive input from the Fourier transform operators 122 associated with the fetal sensors for their channel. Input is also received from the Fourier transform operator or operators 122a and b associated with interference sensors 36.

The operation of frequency domain adaptive cancellers 124 upon the group of Fourier transform spectral coefficients is mathematically described by the equation pair:

$$a_1(n+1) = a_1(n) + (ue_1(n)I_1^*(n)); \text{ and}$$

$$a_2(n+1) = a_2(n) + (ue_2(n)I_2^*(n));$$

where:
- $I_1(n)$ and $I_2(n)$ each represent one of the plurality of Fourier transform complex spectral coefficients associated with the first and second interference Fourier transforms generated by 122a and b;
- $I_1^*(n)$ and $I_2^*(n)$ represent the complex conjugates of $I_1(n)$ and $I_2(n)$, respectively;
- $e_1(n)$ and $e_2(n)$ represent the interference cancelled spectral coefficients produced by frequency domain adaptive cancellers 124 after cancellation of interference sensed by interference sensors 36;
- the quantities $a_1(n)$ and $a_2(n)$ represent a dynamic estimation of the complex transfer coefficient of the interferences in the fetal sensor channels for the corresponding Fourier transform spectral coefficients; and
- n is an index representing the particular Fourier transform spectral coefficient being operated upon.

FIG. 8 shows a preferred digital architecture for performing frequency domain adaptive cancellation operations 124. The incoming Fourier transform spectral coefficients for each channel are each operated upon by a difference operator 125 having a positive input of the incoming spectral coefficient and a subtracted quantity equal to an interference correction value associated with the first interference channel. The first interference channel correction factor is produced by multiplication operator 126. The inputs to multiplication operator 126 include the first interference sensor Fourier transform spectral coefficient corresponding to the fetal sensor Fourier transform spectral coefficient being adaptively corrected. The other factor input to multiplication operator 126 is $a_1(n)$ which is produced as follows.

The output from difference operator 125 is equal to $e_1(n)$ and is multiplied in multiplication operator 127 by the factor u, which is an experimentally derived parameter preprogrammed into the system. The parameter, u, is indicative of the responsiveness of the sensors to fetal heartbeat and interference.

The product $ue_1(n)$ is then multiplied times the complex conjugate of the first interference channel complex spectral coefficient in multiplier 128. The complex conjugate of the first interference channel complex spectral coefficient is produced in complex conjugate operator 129, well known in the art. The resulting product, $ue_1(n) I_1^*(n)$, is summed in addition operator 131 with $a_1(n)$ to produce the quantity $a_1(n+1)$. The quantity $a_1(n+1)$ is stored in shift register 132 for the next following coefficient operation.

A similar operation is performed to correct the Fourier transform coefficients for interference detected by the second interference sensor 36. Difference operator 135, multiplication operators 136-138, complex conjugate operator 139, summation operator 141, and shift register 142 are interconnected and perform the same as 125-129, 131, and 132 described immediately above.

The resulting outputs $e_2(n)$, from frequency adaptive cancellers 124 are the adjusted complex spectral coefficients of the Fourier series corrected to eliminate interference using the dynamically determined transfer function produced for every cycle of the Fourier transform operators 122. In the preferred form of the invention this adaptive correction of the Fourier transform spectral coefficients occurs every ⅛ second and produces a block of 128 complex spectral coefficients.

The outputs from each of the frequency domain adaptive cancellers 124 is input to associated block expansion-accumulation operators 150 for each channel of fetal sensors 35. All the outputs from frequency domain adaptive cancellers 124 are also input to an adaptive channel selector 151. The construction of the adaptive channel selector 151 and components downstream therefrom will be considered first. The discussion will then shift to the block expansion-accumulators 150.

Adaptive channel selector 151 can be any appropriate digital channel selection device having the appropriate number of channel inputs and a separate selection vector input capable of selecting one channel on the basis of the relative fetal heart signal strengths of the fetal sensor channels. Suitable channel selection devices are well known in the art of digital electronics. The actual fetal sensor channel selected and the output from adaptive channel selector 151 is controlled by the relative fetal heart signal strengths presented in vector S as computed by optimum channel weighting system 173 which determines the relative strengths of the channels signals as will be described more fully hereinafter. The channel selected is automatically reassessed in a periodic fashion, such as once every 8 seconds. This reassessment is dependent upon the recalculation of the channel signal strength vector quantities presented in vector S.

The output from adaptive channel selector 151 is in the same form as the input thereto from frequency domain adaptive cancellers 124. The output from channel selector 151 is advantageously input to a frequency weighting filter 153.

Frequency weighting filter 153 takes the block of Fourier transform spectral coefficients and selectively filters the coefficients so as to enhance frequencies associated with the fetal heartbeat. In the case where acoustic sensors 46 are used as fetal sensors 35, it is desirable to selectively eliminate frequencies associated with sounds other than the fetal heart sounds. The fetal heart sounds typically are strongest in the 50-110 Hz range. Accordingly, frequency weighting filter 153 selectively filters the spectral coefficients not associated with these desired frequencies by suppressing or eliminating the strengths of these undesired frequencies, while leaving the chosen frequency range or ranges at full strength. This operation enhances the resulting signal indicating the fetal heart sounds and minimizes noise.

The digital frequency weighting filter 153 is constructed and operated so as to perform a multiplication operation on each of the complex Fourier transform spectral coefficients. The multiplication operation is represented by the equation $$g_{jk}(n) = w_j e_{2jk}(n),$$

where: $e_{2jk}(n)$ represents one of the complex spectral coefficients resulting from one of the frequency domain adaptive cancellers 124; $e_2(n)$ as described with respect to FIG. 8. The additional "k" subscript indicates the specific channel involved and the "j" subscript indicates the particular spectral frequency coefficient being operated upon. The "n" indicates the associated time index or block of Fourier transform spectral coefficients being operated upon. The $w_j$ indicates the preprogrammed weight assigned to the jth spectral frequency and is an experimentally determined value which is relatively large for frequencies of interest, such as 50-110 Hz, and relatively smaller for frequencies which are being suppressed or eliminated. The $g_{jk}(n)$ is the resulting spectral signal value associated with the jth Fourier frequency in the kth sensor channel at time n, and is the output from frequency weighting filter 153. Memory 301 is used to store values for each of the spectral frequency weighting factors, $w_j$. This information is preferably input in filter 153 in the form of a vector W, containing each weight for multiplication as described above.

The specific hardware used to perform the operation of frequency weighting filter 153 is a microprocessor such as 300, programmed to perform such operation in a manner well known in the art of computers and digital processing equipment.

The output from frequency weighting filter 153 is processed by an inverse fast Fourier transform operator (FFT$^{-1}$) 154. Such inverse Fourier transform processors are well known in the art. In a preferred form of the invention, inverse Fourier transform operator 154 processes 128 complex Fourier spectral coefficients every ⅛ second. Only the first 64 output values are accepted and used by the subsequent operators in such preferred embodiment. The output value sequence from inverse Fourier transform operator 154 is a series of digital values in the time domain rather than the frequency domain. In such preferred embodiment the resulting time domain data consists of complex value data points describing the signal as a function of time.

The complex digital output from inverse Fourier transform operator 154 is communicated to a frequency upshift operator 155. Frequency upshift operators 155 is needed because of the parallel frequency downshift operators 112 used to simplify data processing and the change in frequency which resulted therefrom. Frequency upshift operators 155 returns the fetal heart sound signals back to the natural frequency range so that monitoring by people or audio apparatus results in sounds which are familiar to the listener.

Frequency upshift operation 155 and a data rate conversion operation 156 receiving the digital signals from 155, are preferably preformed using microprocessor 300 operating upon the complex, time domain data points. First each data point is processed to determine the rear value of the complex sample. Secondly, the imaginary value of the same complex sample is taken. Third, the negative value is taken of the real part of the next complex data point. And fourthly, the negative value is taken of the same complex sample. The above values are sequentially placed in the resulting output data stream from the frequency upshift operator 155 and data rate convertor 156. This extraction of four values for each complex data point having a real and imaginary component effectively upshifts the resulting time domain frequency such as by 256 Hz, and increases the data stream to a rate of 1024 data points per second in the preferred embodiment, the same as the original preferred sampling rate of A/D convertor 108.

The resulting frequency upshifted and increased data rate information is then converted into an analog signal in a suitable digital-to-analog convertor 157, well known in the art. The resulting analog signal is passed through a suitable analog low pass filter (LPF) 158 and directly presented to telephone jack 81, audio jack 82, or tape jack 83, or presented via suitable amplification (not shown), well known in the art.

The adaptive channel selector 151, frequency weighted filter 153, inverse fast Fourier transform operator 154, frequency upshift operator 155, data rate conversion operator 156, digital-to-analog convertor 156, low pass filter 158 and any associated amplification circuitry are used to provide an audio output signal which can be monitored through a speaker or other suitable audio apparatus so that the mother, father, physician, and other interested individuals can listen.

The discussion immediately following continues the explanation of the automatic signal processing performed for each fetal sensor channel by signal processing circuitry 100. Such automatic signal processing allows warning signals to be automatically provided to the mother via control unit 40.

The output from frequency domain adaptive cancellers 124 go not only to channel selector 151 but also to block expansion-accumulation operators 150. Block expansion-accumulation operators 150 perform a block expansion-accumulation operation on the sets or blocks of 128 complex, interference-cancelled, Fourier transform spectral coefficients processed through frequency domain adaptive cancellers 124. In a preferred embodiment of the invention, the frequency domain adaptive cancellers 124 provide sets of 128 complex spectral coefficients every ⅛ second. The block expansion-accumulation operation advantageously receives 64 different sets over a period of 8 seconds and performs a series of mathematical operations thereon according to the following three equations:

$$P_{0jk} = \sum_{n=1}^{64} e^*_{2jk}(n) \cdot e_{2jk}(n);$$

$$P_{3jk} = \sum_{n=1}^{64} e^*_{2jk}(n) \cdot e_{2jk}(n-3); \text{ and}$$

$$P_{4jk} = \sum_{n=1}^{64} e^*_{2jk}(n) \cdot e_{2jk}(n-4);$$

where: $e_{2jk}(n)$ is the output spectral coefficient from cancellers 124 for the kth channel and for the jth spectral frequency in the particular set of spectral coefficients associated with time or block index n which varies over the 64, or other number, of spectral coefficient blocks over which the summation is being taken; and $e^*_{2jk}(n)$ is the complex conjugate of $e_{2jk}(n)$.

The three summation operations (See FIG. 9 at 164, 166, and 169 defined above are performed on each channel for each spectral coefficient over the relevant number of successive transforms in order to smooth the resulting information for each frequency of the Fourier series as defined by Fourier transforms 122. The resulting information for each channel can be represented as three vectors having, for example, j=128 different smoothed quantities in the preferred embodiment. The resulting first vector, $P_{0k}$ represents the spectral power density in the kth channel for the 8 second period in question. The vector quantities of the first vector, $P_{0k}$, are real because of the multiplication of the complex quantities by their complex conjugates. This reduces the amount of memory needed by one half as compared to the complex quantities resulting in vectors $P_{3k}$ and $P_{4k}$.

The $P_{3k}$ vector represents the average cross-spectral density of the spectral coefficients displaced by a $\frac{3}{8}$ second delay (3 FFT cycles). The $P_{4k}$ vector represents the average cross-spectral density of the spectral coefficients displaced by a 4/8 second delay (4 FFT cycles).

FIG. 9 shows a digital processing structure useful as block expansion-accumulation operators 150. The structure of FIG. 9 receives digitally encoded signal information from the frequency domain adaptive canceller 124 associated with that particular channel. As each of the 128 complex spectral coefficients enter, a complex conjugate operation is performed by complex conjugate operators 162a-c. A first multiplication operator 163 multiplies the complex spectral coefficients by their complex conjugates from 162a and adds the result to a first summation register system 164 having 128 different sums being added and stored. This operation is repeated 64 times as the 64 different Fourier transform coefficients blocks are clocked off. The 128 accumulated sums in summation register system 164 are read out as vector $P_{0k}$.

A three step shift register 365 is interposed between the incoming blocks of coefficients and a second multiplication operator 165. A second summation register system 166 also sums the complex product of $e_{2jk}^*(n)$ and $e_{2jk}(n-3)$ and stores the results into one of 128 different sums being kept.

A single step shift register 167 is interposed between the delayed quantity $e_{2jk}(n-3)$ and a third multiplication operator 168. A third summation register system 169 stores the complex quantities for vector $P_{4k}$.

The three vector outputs from each of block expansion-accumulator operators 150 can be separately communicated or multiplexed to both individual channel frequency weighting filters 170 and to a jointly input average power estimator 171 (see FIG. 6B). The average power estimator 171 receives the spectral power information contained in the $P_{0k}$ vector and is used to provide a best estimate of the signal power in each channel during the block expansion measurement cycle time (such as 8 seconds). The average power estimator takes the spectral power density information in the form of vector $P_{0k}$ and takes the dot product of this vector with the predetermined and preprogrammed spectral weighting vector W. This is represented in the equation:

$$E_k = W \cdot P_{0k} = \sum_{j=1}^{128} w_j P_{0jk};$$

where $E_k$ is a real scaler quantity representing the best estimate of the average power in the kth signal channel during the measurement interval, and W, $w_j$, $P_{0k}$, and $P_{0jk}$ are so explained above. This operation is performed in average power estimator 171 for each individual fetal sensor channel.

The output from average power estimator 171 is a scaler quantity for each channel. This output is communicated to an average power gain adjustment operator 172. Average power gain adjustment operator 172 multiplies each such scaler quantity serving as the estimated average power in that channel, times the gain by which the associated fetal sensor 35 was adjusted by automatic gain control circuits 105. The inputs $G_1 \ldots G_{12}$ are the gain values in the individual 12 channels is represented in FIG. 6A, and are elements of the vector G input to operator 172 shown in FIG. 6B.

The output from operator 172 is a set of gain adjusted, estimated average power values for each channel. These values are input into an optimum channel weighting operator 173. Optimum channel weighting operator 173 dynamically computes the relative strength of the fetal sensor signal in each channel relative to the minimum signal contained in the channel having the weakest signal. This is done according to the following equation:

$$S_k = (E_{Ak} - E_{min})/E_{min};$$

where
  $S_k$ is the strength factor being calculated which is indicative of the relative signal-to-noise in that channel;
  $E_{Ak}$ is the gain adjusted average power estimate from 172 for the kth channel; and $E_{min}$ is the minimum value of gain adjusted average power amongst all of the k channels. The values $S_k$ are used in the adaptive channel weighting filter 174 (see FIGS. 6B and 10) which is used to weight the individual channel signals, as will be explained more fully below.

The $P_{3k}$ and $P_{4k}$ vector outputs from the channel block expansion-accumulation operations 150 are input to parallel frequency weighting filters 170 for each channel (see FIG. 6B). The frequency weighting filters 170 multiply the predetermined preprogrammed spectral weighting factors $w_j$ contained in vector W by the spectral average power densities defined by vectors $P_{3k}$ and $P_{4k}$, according to the following equations:

$$P'_{3jk} = w_j P_{3jk}; \text{ and}$$

$$P'_{4jk} = w_j P_{4jk};$$

where $w_j$, $P_{3jk}$ and $P_{4jk}$ are as defined above, and $P'_{3jk}$ and $P'_{4jk}$ are the frequency filtered output quantities from filters 170.

The output quantities from filters 170 are input to inverse fast Fourier transform operators (FFT$^{-1}$) 175 (see FIG. 6B. Inverse Fourier transform operators 175 perform an inverse Fourier transformation upon the two complete blocks of filtered complex spectral values. In the preferred embodiment, each vector $P_{3k}$ and $P_{4k}$ have 128 complex values. Each is transformed from frequency domain back into time domain in the form of vectors having 128 complex values each. The remaining signal processing components use only 64 of the 128 complex values transformed for each block of vector values, thus requiring that 128 complex values be processed for both.

The outputs from inverse Fourier transform operators 175 are input to parallel magnitude detection units 176. Magnitude detection units 176 convert the complex time domain signal values into real total magnitude quantities according to the well known formula $r = (a^2 + b^2)^{\frac{1}{2}}$; where r is the resultant real total magnitude value; a is the magnitude of the real component of the complex value; and b is the magnitude of the imaginary component of the complex value. The preferred form of the invention thus determines the total magnitudes of 128 complex pairs from vectors $P_{3k}$ and $P_{4k}$. The output sequence from magnitude detectors 176 are advantageously viewed as vectors $R_k$ having 128 real values, per channel.

The different channel vectors $R_k$ are all separately input into adaptive channel weighting filter 174. The function of adaptive channel weighting filter 174 is to combine the fetal sensor channel values and balance the relative weighting given to each channel, based upon the $S_k$ values determined by optimum channel weighting operator 173. The $S_k$ values are an estimate of the signal-to-noise ratio since the strongest channel signal is compared to the weakest channel signal which is predominantly noise. The weight given to the weakest signal channel is zero and to the strongest channel is one. Other channels are given strength values lying between these values. FIG. 10 illustrates that the adaptive channel weighting filter 174 combines the fetal sensor channel signals according to the following equation:

$$T_1 = \sum_{k=1}^{K=12} S_k R_{1k};$$

where: $T_1$ is the resultant digital signal value at point or time 1 of the time domain sequence; such one point is one of the 128 points generated for the 8 second interval in the preferred embodiment; $S_k$ is as defined above and $R_{1k}$ is the real scaler quantity associated with the kth channel at point 1 of the digital signal values.

FIG. 10 illustrates a preferred form of digital architecture for accomplishing the operation of adaptive channel weighting filter 174. Filter 174 includes a plurality of multipliers 177 individually associated with each of the 12 or so fetal sensor channels. Multipliers 177 multiply the signal channels by the associated signal strength quantity $S_1-S_{12}$ for channels 1-12, respectively. The outputs from multipliers 177 are summed together in summation operator 178 to produce the output digital signal. The signal output is at the rate of 128 values per 8 second time interval, the same as the output from magnitude detectors 176. $T_1$ thus provides a resultant signal indicating the fetal heart amplitude as derived from a combination of fetal sensors 35 and by selectively using the most beneficial frequencies and sensors, and by cancelling interfering noise detected by interfering sensors 36. The $T_1$ value is recalculated to a new value every 1/16 second thus giving good resolution of fetal heart contractions.

Signal processing system 100 is further provided with several diagnostic subsystems for automatically analyzing and communicating the status of the fetus according to certain preprogrammed parameters or criteria. One such subsystem is the breech position analyzer 180 which receives the S vector values produced by optimum channel weighting operator 173 every measurement period (8 seconds in the preferred embodiment). The S vector values indicative of the signal strength in each of the channels, are compared to preprogrammed known value ranges which are statistically known to indicate the fetus is in a breech position versus normal fetal position. The specific algorithm used to set the ranges and relative strength of the channel signals may vary but will typically identify certain fetal sensor channels which are most reliable in sensing higher or lower relative signal levels as a result of a breech positioning of the fetus. For example, sensors 35 in the upper row of the sensor belt 30 may provide a statistically higher signal level when the fetus is in a breech position. Breech position analyzer receives the S vector values from optimum channel weighting operator 173 and also receives threshold values in the form of vector $S_t$ from an appropriate digital memory such a 301. Satisfaction of the conditions causes breech position analyzer 180 to produce an output to alarm light 76a and to audio alarm 78.

A further diagnostic or analytical subsystem included in signal processing system 100 is directed to performing a diagnostic test for fetal well-being which is commonly referred to as the fetal non-stress test. Conceptually, the non-stress test involves sensing movement of the fetus and examining the fetal heart rate immediately thereafter to determine whether an acceptable increase or acceleration in the fetal heart rate has occurred. The specific numbers used as parameters of the test are open to somewhat different medical interpretations. One set of parameters is advantageously defined to require a 15 second fetal heart rate acceleration cycle having at least 15 beats per minute in excess of a measured baseline fetal heart rate. Failure of the fetus to properly react may indicate fetal distress due to a variety of causes.

Signal processing system 100 is adapted to receive a signal from a suitable fetal movement detector 182 (FIG. 6C) which can advantageously be one or more accelerometers 47 described above, or alternatives thereto such as the moving coil fetal movement sensor described in the article cited above to David Adler and Yona Mahler. Single or multiple alternative fetal movement detectors are also possible with suitable modification to signal processing system 100 to enable proper fetal movement signal interpretation.

The non-stress test subsystem 181 included in signal processing system 100 receives digital information from adaptive channel weighting filter 174 in the form of a string of values. In the preferred embodiment there are 128 real values associated with each period of 8 seconds. This information is communicated to a first peak value processor 183. Peak value processor 183 identifies peak signal values in the output from channel weighting filter 174. The identified peaks are recognized as a digital location in the string of signal values and the time spacing and fetal heart rate are calculated therefrom by peak value processor 183. The calculated fetal heart rate is digitally encoded as signal h and communicated to a fetal heart rate display 73, which can be a liquid crystal, light emitting diode or other suitable display, well-known in the art.

The resulting digitally encoded information of the fetal heart rate, h, is also communicated to comparison circuit 185 which compares the fetal heart rate information h to a threshold value t which is preprogrammed in memory. Threshold value t is advantageously 135 beats per minute, a medically determined minimum for fetal heart rate accelerations under the fetal non-stress test. If comparison circuit 185 is activated by fetal heart rate in excess of threshold t, then a pulse is sent to event interpreter 186. If one or more pulses are received during a predetermined period, having a duration such as 3 measurement cycles (24 seconds), then an event is declared and an output pulse signal e is communicated to a counter 187. Counter 187 counts the number of pulse signals e and if the number of pulses counted exceed a count threshold f within a predetermined preprogrammed period defined by parameter g of coincidence detector 188 then the test for the given predetermined period is passed. Parameter g is advantageously 40 minutes. The counter is reset at the end of each such test period g. If the threshold number of event pulses do not occur within the predetermined counter period then an output signal p is provided by counter 187 to coincidence detector 188 for coincidence comparison to the fetal movement information from fetal movement detector 182.

Coincidence detector 188 receives input from comparison circuit 199 which compares the output from fetal movement detector 182 with a threshold value q and provides an output signal r when fetal movement has been sensed during the relevant measurement period. If fetal movement has not occurred then signal r is not present and coincidence detector 188 does produce an output signal. If fetal movement has occurred then signal r is output to coincidence detector 188. Detector 188 produces an output signal when signals p and r are both present, which lights alarm light 76c and audio alarm 78, thus indicating failure of the fetal non-stress test.

Comparison circuit 199 provides a "no" output signal u if no fetal movement is detected within the measurement period. This signal is communicated to a second coincidence circuit 201. Coincidence circuit 201 is triggered if there is no fetal movement detected during a predetermined preprogrammed period of time set by input v, such as 80 minutes. If no movement occurs during such period v, then an output signal is communicated from coincidence circuit 201 to alarm light 76b and to audio alarm 78.

The output sequence of digital signal values from channel weighting filter 174 is also communicated to an accumulator 210. Accumulator 210 receives the output sequence and sums the values for each sequence entry over a span of four separates to further smooth the fetal heart rate information. The summed totals for all summed sequence entries are then output into a peak value processor 211 and the accumulation registers are then zeroed. The peak value processor 211 converts the data sequence, such as 128 digital values, into an average measure of fetal heart rate during a period defined by 4 measurement periods (as defined by the block expansion accumulator 150). The resulting averaged fetal heart rate information d is then compared to upper and lower threshold values x and z in comparison circuits 212 and 213, respectively. An upper threshold value x of, for example, 160 beats per minute, provides an effective analytical subsystem for diagnosing sustained fetal trachycardia syndrome (sustained excessive fetal heart rate). A fetal heart rate value d below the lower threshold z causes comparison circuit 213 to have an output which lights alarm light 76e and powers audio alarm 78. A fetal heart rate value d in excess of threshold x causes comparison circuit 212 to have an output which lights alarm light 76d and powers audio alarm 78. The desired threshold values x and z are clearly subject to variations and are preprogrammed into memory and adjustable therein.

Peak value processor 211 also provides an output b which is the maximum value in the accumulated and average sequence produced by accumulator 210. This peak signal strength is correlated in normalizer 220 with the total power in all channels during a 32 second period weighted by the $E_A$ vector channel strength factors. The equation representing such correlation C is $$C = )/P_T$$

where $$P_T = \sum_{n=1}^{4} \sum_{k=1}^{10} S_k E_{Ak}(n)$$

is the total power; and

R max is the maximum sequence value; the remaining symbols are defined as hereinabove.

Correlation factor C is compared in comparison circuit 214 to a preprogrammed threshold correlation value C' which is useful in discriminating between multiple fetuses and single fetus based upon a relatively lower correlation when two fetuses are present as compared to empirically determined correlations with a range of single fetuses. If correlation factor C is less than threshold C' then an output signal from comparison circuit 214 lights alarm light 76f and operates audio alarm 78.

FIG. 6C also shows a personal computer 230 which can be connected to fetal monitoring system 20 via jack 80 in order to monitor the output sequence of values from adaptive channel weighting filter 174. This information can then be analyzed on the physician's personal computer using a variety of suitable data processing programs to provide improved diagnostic analysis of the fetal heart signals. Computer 230 can also be used to input patient information and to program analytical parameters.

The fetal monitoring system of this invention described above is used by installing the sensor belt 30 and associated sensors 35 and 36 as appropriate to perceive fetal and interference signals as described above. The control unit 40 is then connected to sensors 35 and 36 and the signal processing functions described above are initiated on a continuous and automatic basis.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

I claim:

1. An ambulatory, non-invasive, automatic fetal monitoring system for use on a mother to continuously measure and analyze information indicative of the well-being of a fetal living within the mother, comprising:

a sensor garment for wear by the mother about the mother's torso;

a plurality of fetal cardiac sensor means mounted on said sensor garment at spaced locations to continuously detect fetal heartbeats when the fetus is in a variety of positions within the mother and provide electronic fetal cardiac sensor signals at least one of which is indicative of fetal heartbeats with time;

at least one fetal movement sensor means mounted on said sensor garment to continuously detect physical movement of the fetus within the mother and provide at least one electronic fetal movement sensor signal which is indicative of fetal movement;

a computing means connected to receive and analyze said cardiac and movement sensor signals to determine fetal heart rate and including means to perform at least one analysis relating fetal heart rate and detected movement by the fetus;

heart rate indicator means for indicating fetal heart rate; and means for indicating results of the analysis relating fetal heart rate and detected movement by the fetus.

2. The automatic fetal monitoring system of claim 1 wherein the fetal cardiac sensors are electrocardiographic sensors.

3. The automatic fetal monitoring system of claim 1 wherein the fetal cardiac sensors are acoustical sensors.

4. The automatic fetal monitoring system of claim 1 further comprising adaptive signal cancellation means for adaptively cancelling at least a portion of at least one cardiac sensor signal to increase the strength of signals indicative of fetal heartbeats.

5. The automatic fetal monitoring system of claim 1 further comprising adaptive signal cancellation means for adaptively cancelling at least a portion of at least one cardiac sensor signal to increase the strength of signals indicative of fetal heartbeats, said adaptive signal cancellation means including at least one sensor means which is mounted to selectively sense interfering signal components sensed by the fetal cardiac sensor means.

6. The automatic fetal monitoring system of claim 5 wherein the adaptive signal cancellation means includes sound sensors mounted on said sensor belt which provide signals which are used to adaptively cancel extraneous noise portions of the plurality of cardiac sensor signals in order to emphasize fetal cardiac signal portions thereof.

7. The automatic fetal monitoring system of claim 1 wherein there are a plurality of fetal movement sensor means arranged at spaced positions on said sensor garment to detect fetal movements when the fetus is in a variety of positions within the mother.

8. The automatic fetal monitoring system of claim 7 wherein the sensor garment is a belt having a girth which extends about the torso of the mother, and an enlarged abdominal area for extending over the mother's abdomen; and wherein a plurality of said cardiac and movement sensor means are mounted within the enlarged abdominal area for sensing adjacent to the mother's abdomen.

9. The automatic fetal monitoring system of claim 8 further comprising a control unit which incorporates said computing means and said means to perform at least one analysis relating fetal heart rate and detected movement by the fetus; and wherein the sensor garment detachably mounts the control unit.

10. The automatic fetal monitoring system of claim 8 wherein the sensor garment is made from a stretchable material.

11. The automatic fetal monitoring system of claim 1 further comprising:

memory means electrically connected to transmit data to the computer means and for storing health related information relating to the mother or fetus; and display means electrically connected to the memory means, for allowing stored health related information to be visually displayed.

12. The automatic fetal monitoring system of claim 1 further comprising breech position analyzer means electrically connected to the computer means for analyzing the relative strength of signals produced by the plurality of fetal cardiac sensors and for providing a breech position signal; and breech position indicating means for indicating when the breech position analyzer has produced a breech position signal indicative of increased probability that a fetus is in a breech position.

13. The automatic fetal monitoring system of claim 1 further comprising sustained absence of fetal movement analyzer means for analyzing to determine whether the fetal movement sensor has failed to detect fetal movement for a predetermined period of time, and means for indicating that no fetal movement has been sensed for such predetermined period of time.

14. The automatic fetal monitoring system of claim 1 further comprising means for comparing fetal heart rate information to at least one preprogrammed threshold; and indicator means for indicating that fetal heart rate information is outside of the preprogrammed threshold.

15. The automatic fetal monitoring system of claim 1 further comprising a multiple fetus analyzer means electrically connected to the computer means for analyzing the relative strengths of fetal cardiac sensor signals from the plurality of fetal cardiac sensor means; and multiple fetus indicator means electrically connected to said multiple fetus analyzer means for indicating increased probability that multiple fetuses are present in the mother.

16. The automatic fetal monitoring system of claim 1 further comprising:

memory means electrically connected to transmit data to said computer means for storing health related information relating to the motor or fetus;

display means electrically connected to the memory means for allowing stored health related information to be visually displayed;

breech position analyzer means electrically connected to the computer means for analyzing the relative strength of signals produced by the plurality of fetal cardiac sensors and providing a breech position signal;

breech position indicating means for indicating when the breech position analyzer has produced a breech position signal indicative of increased probability that a fetus is in a breech position;

sustained absence of fetal movement analyzer means electrically connected to the computer means for analyzing to determine whether the fetal movement sensor has failed to detect fetal movement for a predetermined period of time, and means for indicating that no fetal movement has been sensed for such predetermined period of time;

means for comparing fetal heart rate information to at least one preprogrammed threshold; and indicator means for indicating that fetal heart rate information is outside of the preprogrammed threshold; and multiple fetal analyzer means electrically connected to the computer means for analyzing the relative strengths of fetal cardiac sensor signals from the plurality of fetal cardiac sensor means; and multiple fetus indicator means electrically connected to said multiple fetus analyzer means for indicating increased probability that multiple fetuses are present in the mother.

17. An ambulatory, non-invasive, automatic fetal monitoring system for portable use on a mother to continuously measure and analyze information indicative of the well-being of a fetus living within the mother, comprising:
- a plurality of fetal cardiac sensor means for detecting fetal heartbeats when the fetus is in a variety of positions within the mother and providing a plurality of electronic fetal cardiac sensor signals which are indicative of fetal heartbeats as perceived from the plurality of fetal cardiac sensor means;
- at least one fetal movement sensor means for detecting physical movement of the fetus within the mother and providing an electronic fetal movement sensor signal which is indicative of fetal movement;
- a sensor belt for extending about a torso of the mother and positioning the plurality of fetal cardiac sensors and the at least one fetal movement sensor in close proximity to the mother's abdomen when the sensor belt is properly worn;
- a digital system including at least one microprocessor means and memory means for analyzing said cardiac and movement sensor signals to determine fetal heart rate and including means for analyzing whether fetal heart rate has accelerated immediately after movement by the fetus; and
- fetal heart rate indicator means for indicating fetal heart rate; and
- indicator means for indicating whether fetal heart rate has accelerated immediately after fetal movement.

18. The automatic fetal monitoring system of claim 17 further comprising:
- programmable means for storing health related information concerning the mother or fetus in said memory means; and
- display means electrically connected to said memory means for allowing stored health related information to be visually displayed.

19. The automatic fetal monitoring system of claim 17 further comprising breech position analyzer means for analyzing the relative strength of signals produced by the plurality of fetal cardiac sensors and for providing a breech position signal; and breech position indicating means for indicating when the breech position analyzer has produced a breech position signal indicative of increased probability that a fetus is in a breech position.

20. The automatic fetal monitoring system of claim 17 further comprising a sustained absence of fetal movement analyzer means for analyzing to determine whether the fetal movement sensor has failed to detect movement for a predetermined period of time, and means for indicating that no fetal movement has been sensed for such predetermined period of time.

21. The automatic fetal monitoring system of claim 17 further comprising means for comparing fetal heart rate information to at least one preprogrammed threshold; and indicator means for indicating that fetal heart rate information is outside of the preprogrammed threshold.

22. The automatic fetal monitoring system of claim 17 further comprising a multiple fetal analyzer means electrically connected to the computer means for analyzing the relative strengths of fetal cardiac sensor signals from the plurality of fetal cardiac sensor means; and multiple fetus indicator means electrically connected to said multiple fetus analyzer means for indicating increased probability that multiple fetuses are present in the mother.

23. A non-invasive, automatic multiple fetus monitoring system for continuous use on a mother to indicate a likelihood that multiple fetuses are present within the mother, comprising:
- a sensor garment for wear by the mother about the mother's abdomen;
- a plurality of fetal cardiac sensor means mounted on said garment at spaced locations to continuously detect fetal heartbeats when the fetus is in a variety of positions within the mother and provide electronic fetal cardiac sensor signals which are indicative of fetal heartbeats with time;
- a computing means connected to receive and analyze said fetal cardiac sensor signals; said computing means including memory means and means for comparing measured fetal cardiac sensor signal strengths from the plurality of fetal cardiac sensors against preprogrammed criteria indicating an increased likelihood of multiple fetuses; and
- multiple fetus indicator means for indicating increased probably that multiple fetuses are present.

24. A multiple fetus monitoring system according to claim 23 and further comprising adaptive signal cancellation means for adaptively cancelling at least a portion of at least one of said cardiac sensor signals to increase the strength of signals indicative of fetal heartbeats.

25. A multiple fetus monitoring system according to claim 23 and further comprising adaptive signal cancellation means for adaptively cancelling at least a portion of at least one cardiac sensor signal to increase the strength of signals indicative of fuel heartbeats, said adaptive signal cancellation means including at least one sensor means which is mounted to selectively sense interfering signal components sensed by the fetal cardiac sensor means.

26. A multiple fetus monitoring system according to claim 25 wherein said means for comparing measured fetal cardiac sensor signal strengths from the plurality of fetal cardiac sensors against preprogrammed criteria performs an analysis which indicates relatively lower correlation of fetal heartbeats to a preprogrammed threshold correlation value.

27. A non-invasive, automatic breech position detector for continuous use on a mother to indicate a likelihood that a fetus has assumed a breech position in the mother's womb, comprising:
- a sensor garment for wear by the mother about the mother's abdomen;
- a plurality of fetal cardiac sensors mounted on said sensor garment at a plurality of spaced positions for detecting fetal heartbeats and providing electronic fetal cardiac sensor signals;
- computing means electrically connected to receive and analyze said fetal cardiac sensor signals; said computing means including memory means and means for analyzing said fetal cardiac sensor signals to compare measured fetal cardiac sensor signal strength against preprogrammed criteria indicating an increased likelihood of breech position for at least one combination of relative signal strengths for the plurality of cardiac sensor signals, and for producing a breech position signal; and
- breech position indicator means for indicating when the breech position signal has been produced.

28. An automatic breech position detector according to claim 27 and further comprising adaptive signal cancellation means for adaptively cancelling at least a portion of at least one fetal cardiac sensor signal to increase the strength of signals indicative of fetal heartbeats.

29. An automatic breech position detector according to claim 36 and further comprising a multiple fetus monitoring system according to claim 32 and further comprising adaptive signal cancellation means for adaptively cancelling at least a portion of at least one cardiac sensor signal to increase the strength of signals indicative of fetal heart beats, said adaptive signal cancellation means including at least one sensor means which is mounted to selectively sense interfering signal components sensed by the fetal cardiac sensor means.

* * * * *